United States Patent

Alcorn et al.

[11] Patent Number: 5,107,859
[45] Date of Patent: Apr. 28, 1992

[54] FLUID COLLECTION BAGS WITH FOAM SUPPORT INSERTS

[75] Inventors: Dennis R. Alcorn; Robert E. Delk, both of Dallas, Tex.

[73] Assignee: Struckmeyer Corporation, Dallas, Tex.

[21] Appl. No.: 562,933

[22] Filed: Aug. 6, 1990

[51] Int. Cl.⁵ .............................................. A61F 13/00
[52] U.S. Cl. .................................. 128/853; 128/849; 604/356; 604/408
[58] Field of Search .............................. 128/849–853; 604/356, 408

[56] References Cited

U.S. PATENT DOCUMENTS

| | | | |
|---|---|---|---|
| 3,347,226 | 10/1967 | Harrower | 128/850 |
| 3,397,692 | 8/1968 | Creager, Jr. et al. | 128/850 |
| 3,763,857 | 10/1973 | Schrading | 128/853 |
| 4,489,720 | 12/1984 | Morris et al. | 128/853 |
| 4,559,937 | 12/1985 | Vinson | 128/853 X |
| 4,616,642 | 10/1986 | Martin et al. | 128/853 |
| 4,869,271 | 9/1989 | Idris | 128/853 |
| 4,890,628 | 1/1990 | Jackson | 128/849 |

Primary Examiner—Robert A. Hafer
Assistant Examiner—Kerry Owens
Attorney, Agent, or Firm—Richard C. Litman

[57] ABSTRACT

A fluid collection bag is disclosed which has a corrugated foam opening support. The foam support is placed continuously around the opening to automatically keep the fluid collection bag in the correct open position. The corrugations on the foam support allow for continuous fluid accumulation and/or drainage. A solid foam bar is also utilized as an opening support. The foam bar is specifically shaped to continuously force the fluid collection bag into the proper open position. A pressure sensitive adhesive layer is placed on the bottom of the bag to keep the fluid collection bag in the proper positon on the patient, and to maintain a fluid imprevious seal between the surgical site and the patient and/or medical staff.

7 Claims, 4 Drawing Sheets

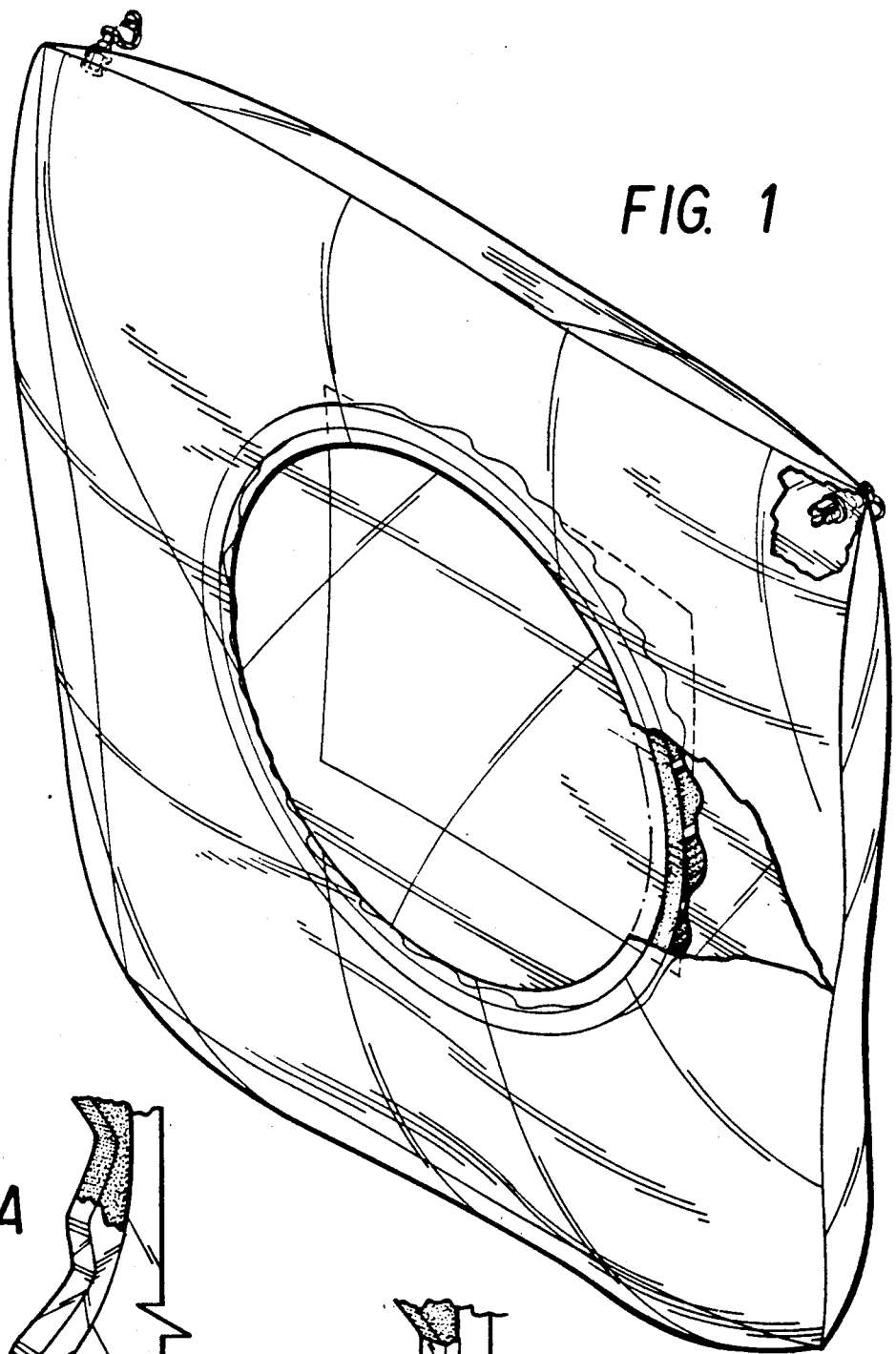
FIG. 1
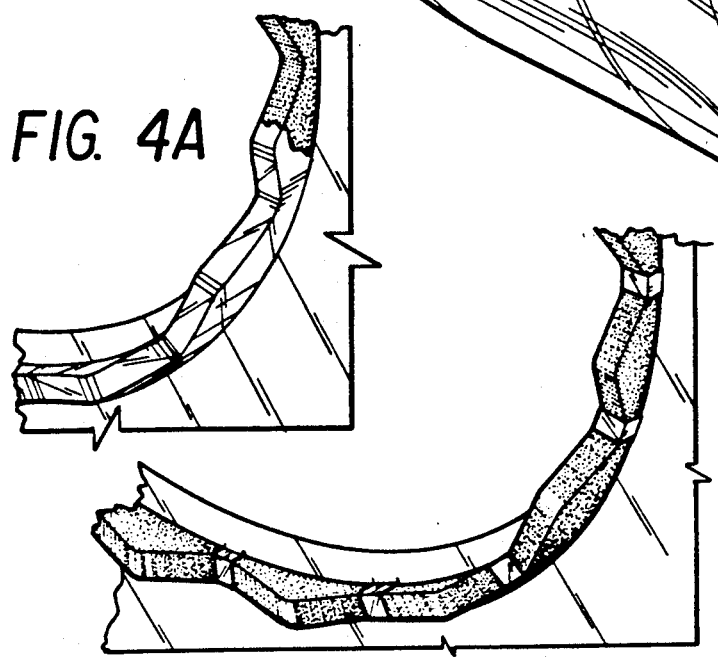
FIG. 4A
FIG. 4

FLUID COLLECTION BAGS WITH FOAM SUPPORT INSERTS

FIELD OF THE INVENTION

The present invention relates generally to fluid collection bags for surgical procedures and, more particularly, to fluid collection bags with foam support inserts wherein the foam is shaped to automatically keep the fluid collection bags in the correct open position.

BACKGROUND OF THE INVENTION

A patient undergoing a surgical procedure is generally at least partially covered by a surgical drape and/or a fluid collection bag. The surgical procedure is often performed through a fenestration or opening in the drape. The drape performs several functions during the operation. Surgical drapes are sterilized prior to use so that the drape provides a protective barrier between the nonsterile patient and operating table and the sterile clothing of the surgeon. Single use, disposable surgical drapes are commonly used; such drapes generally are sterile and prefolded in a protective package, ready for draping over the patient.

Another function of surgical drapes is to disperse fluid runoff from the surgical site so that it does not obstruct the working of the surgeon and so that it does not soil the patient. If there is only a small amount of fluid runoff from the surgical site, it may be simply dispersed across the surface of the drape; some drapes are produced with an absorbent upper surface in order to absorb such fluid runoff. Where a substantial amount of fluid runoff is expected from the surgical site, means for channeling that fluid into an appropriate receptacle may be provided by the drape. Such drapes are disclosed in U.S. Pat No. 759,084 issued to Eggers et al. and U.S. Pat. No. 3,650,267 issued to Anderson.

Drapes may have pouches built into or attached to the drapes in order to capture fluid runoff from the surgical site. Drapes with such pouches are disclosed in U.S. Pat. Nos. 3,791,382 and 4,323,062 issued to Collins and Canty respectively.

A large amount of fluid runoff from the surgical site is often associated with crainiotomy and Caesarean section surgery. Fluid collection reservoirs may be formed integrally with such drapes in order to capture such fluid runoff. Fluid collection drapes for crainiotomy procedures are disclosed in U.S. Pat. No. 4,559,937 issued to Vinson and U.S. Pat. No. 4,598,458 issued to McAllester.

DESCRIPTION OF RELATED ART

The broad concept of providing a surgical drape or fluid collection bag with openings and foam supports is generally known. The supports for the openings in a surgical drape commonly consist of an elastic band, a plastic coated wire or a foam type material. Ideally, these support bands will keep the apertures in the open position so the surgeon has an undisturbed and uncluttered access to the work area. The support bands should also retain and direct fluid runoff into appropriate reservoirs or fluid drainage tubes.

U.S. Pat. No. 3,650,267 issued to Anderson discloses such a surgical drape with an elastic support for the surgical drape opening. Referring to the drawings in this patent, elastic band 18 surrounds the opening 14. A hole 26 is present in the bottom of the drape to allow for access into the work area. As fluid enters into the drape it is directed to and is removed by dis-charge tube 24. While this design works well under ideal conditions, it does have some drawbacks. If the rim containing elastic band 18 falls or collapses onto the bottom wall 10, fluid may be prevented from entering the discharge tube. This could lead to a condition where fluid overflows the rim 18 and contacts and contaminates the surgeon and/or the patient.

U.S. Pat. No. 4,869,271 issued to Idris discloses a surgical drape that utilizes plastic coated soft metal strips for the opening support. The metal strips must be hand formed to keep the pouch in the proper open position. Although this design works well for its intended purpose, the soft metal support must often be reformed during the course of the surgical procedure, to maintain the correct opening configuration.

U.S. Pat. Nos. 4,559,937 and 4,598,458 issued to Vinson and McAllester respectively disclose surgical drapes with fluid collection bags and foam material opening means for crainiotomy surgical procedures. These patents disclose the use of a foam rod to keep the opening of the surgical drape in an open position. However, no provision is made to allow for fluid flow underneath the foam support rod in case it comes into contact with the bottom portion of the drape.

None of the above listed patents are seen to disclose the specific arrangement of concepts disclosed by the present invention.

SUMMARY OF THE INVENTION

By the present invention an improved fluid collection bag with a foam support ring or bar is provided. For fluid collection bag to function properly it must remain in an open position. It is common, during the course of a surgical procedure, for a section of the bag to collapse. This might be due to physical contact by a person assisting in the operation, the surgeon himself or just by the natural forces of gravity. When this condition occurs the top portion, or the sidewall, of the fluid collection bag collapses and makes contact with the bottom portion of the bag. When the bag is in the normal open position fluid will pass along the bottom surface of the bag and be accumulated or drained by a fluid discharge tube. When a portion of the sidewall collapses, fluid will accumulate at the site of the collapse. The sidewall functions as a dam, and will cause the fluid to overflow unless the situation is corrected.

By the present invention, a foam support ring or bar is provided to overcome the previously mentioned difficulties. The use of a foam type material has many advantages over plastic coated soft metal wire. Wire can break and perforate the bag, which may result in injury to the patient and/or medical staff. This condition is eliminated by using foam. Wire must also be hand formed time and again during the surgical procedure. In the present invention the foam is manufactured so it has a "memory". It will automatically reform to its original shape. The present invention also incorporates a corrugated surface into the foam support ring. Even if the sidewall of a fluid collection bag collapses, the corrugations in the foam will provide channels, or built-in passageways, for the fluid, thereby maintaining proper fluid drainage.

Accordingly, one of the objects of the present invention is to provide an improved fluid collection bag with a foam support ring or rod.

Another object of the present invention is to provide an improved fluid collection bag with a continuous foam support ring, and with corrugations to allow for continuous fluid drainage.

A further object of the present invention is to provide an improved fluid collection bag wherein the foam support has a "memory" and will automatically keep the fluid collection bag in the proper open position.

A still further object of the present invention is to provide an improved fluid collection bag which prevents the possibility of having a wire break, project out into the surgical site, and injure the patient and/or medical staff.

Yet another object of the present invention is to provide fastening means, which include nonwoven flexible fabric bands and/or adhesive means, to affix the foam support to the fluid collection bag.

A further object of the present invention is to provide a fastening means which envelope the foam support in a flexible, fluid impervious sheet material.

An additional object of the present invention is to provide a two layer wall structure for the fluid collection bag, to increase abrasion, puncture and tear resistance.

A further object of the present invention is to provide a pressure sensitive adhesive layer on the bottom of the bag to secure the fluid collection bag to the patient, and to function as a fluid impervious seal between the surgical site and the patient and/or medical staff.

With these and other objects in view which will more readily appear as the nature of the invention is better understood, the invention consists in the novel combination and assembly of parts hereinafter more fully described, illustrated and claimed with reference being made to the attached drawings.

BRIEF DESCRIPTION OF THE DRAWINGS

FIG. 1 is a top perspective view of a Caesarean section fluid collection bag, with sections of the bag removed to show the various features.

FIG. 4 is an enlarged perspective view in section of the foam support ring, and one embodiment of securing the form ring to the fluid collection bag.

FIG. 4a is an enlarged perspective view in section of the foam support, and an alternate embodiment of securing the foam support to the fluid collection bag.

Similar reference characters designate corresponding parts throughout the several figures of the drawings.

DETAILED DESCRIPTION OF THE PREFERRED EMBODIMENTS

Figure 2:
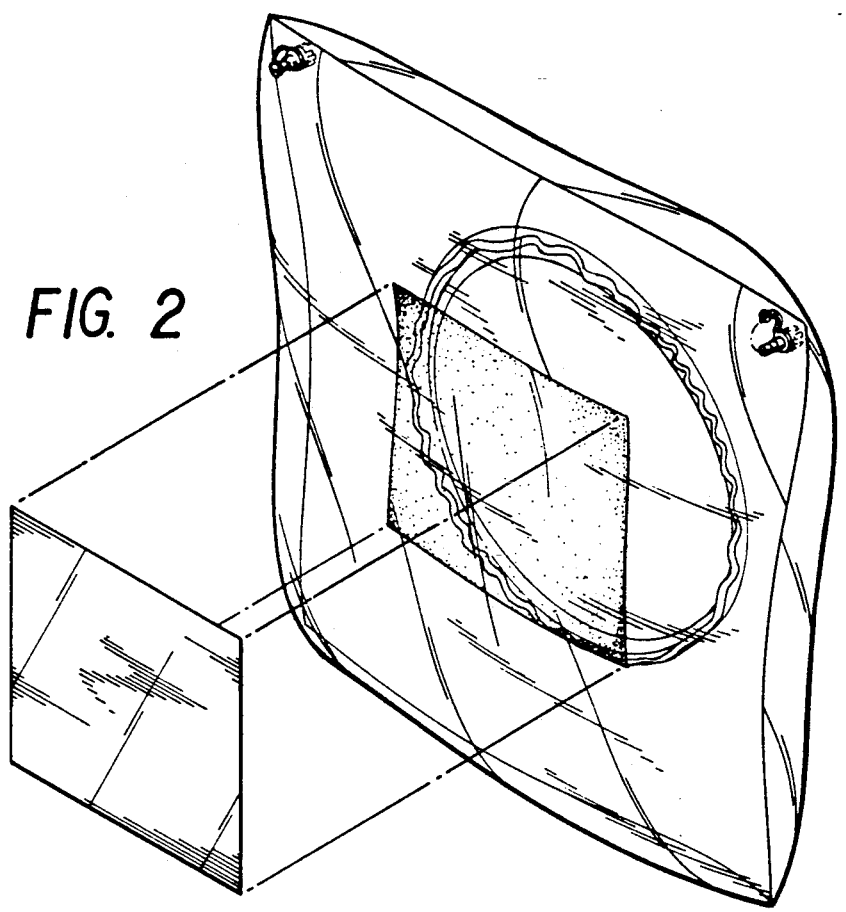
FIG. 2 is a bottom perspective view of the fluid collection bag with the release paper shown in exploded format.
Figure 3:
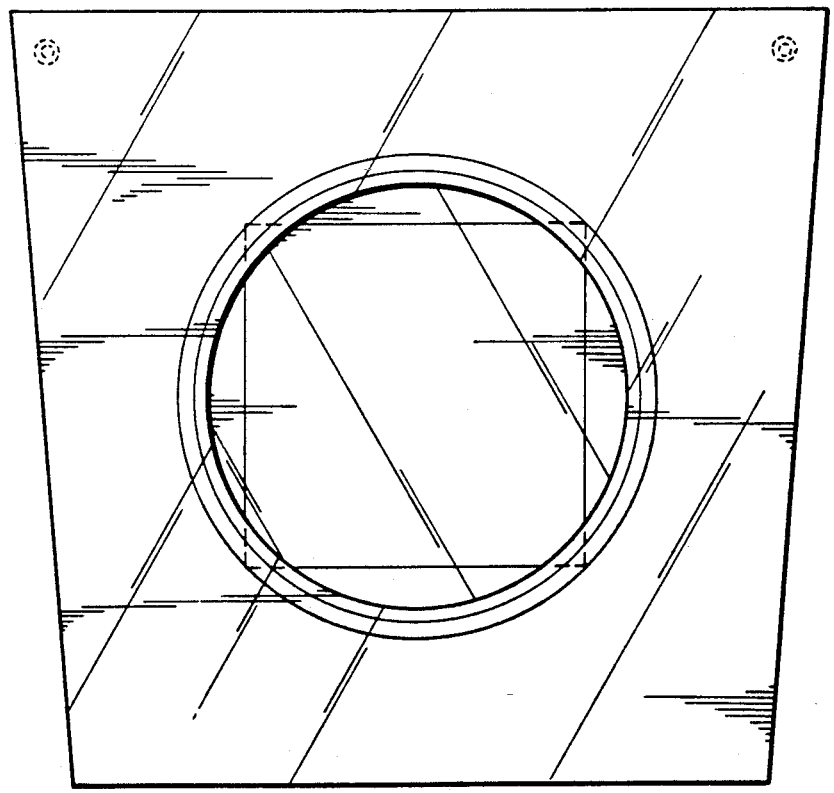
FIG. 3 is a top view of the fluid collection bag of the present invention.

Referring now to the drawings, particularly to FIG. 1 the present invention will be understood to relate to an improved fluid collection bag, generally referred to by the numeral 10, which is particularly adapted for use in Caesarean section surgical procedures, with particular improvements in the foam support ring 12. Base sheet 14 contains the surgical site 16 and fluid discharge ports 18. The base sheet 14 and sidewall sheet 20 are constructed of a nonwoven fabric laminate such as a typical surgical grade plastic sheet or clean medical grade polyethylene film. Base sheet 14 is bonded to sidewall sheet 20 along seam 22. By using two separate sheets 14 and 20, a double walled sidewall sheet 20 may be incorporated in the structure of the fluid collection bag 10. The double walled structure for sidewall 20 is preferred because it will increase the puncture and tear resistance of the bag in the upper portions. The upper portions of the bag experience the greatest abrasion and possibility for damage during the course of the surgical procedure.

Fluid collection bag 10, in the embodiment designed for a Caesarean section, is typically rectangular with preferred dimensions of 30.0 inches (+/-0.5") in height by 32.0 inches (+/-0.5") in width. Located in sidewall sheet 20, is an opening 24, which preferably has a diameter of 16.0 inches (+/-0.5"). The opening 24 gives the surgeon access to the surgical site 16. On the bottom of the base sheet 14 there is a pressure sensitive adhesive layer 26, corresponding to the surgical site 16, which is preferably 13.0 inches by 13.0 inches (+/-0.5"). Prior to use of the fluid collection bag 10, the adhesive layer is covered by a release paper 28, which is preferably 18.0 inches by 18.0 inches (+/-0.5"). The fluid drainage ports 18 are preferably located 2.0 inches (+/-0.5") from the corners 30.

The pressure sensitive adhesive 26 is used to adhere the fluid collection bag 10 securely to the patient. This prevents fluid runoff from the surgical site between the patient and base sheet 14. The adhesive has qualities that allow for easy application and removal from the skin of the patient.

Fluid collection bag 10, which is shown in an alternate perspective view in FIG. 2, is preferably constructed of a flexible, fluid-impervious sheet material, more preferably of an inexpensive material such as surgical grade plastic sheet or clear medical grade polyethylene film. It is preferred that the fluid collection bag 10 be made of a substantially clear material to allow inspection of collected fluid through the bag material. The preferred thickness for the clear polyethylene film is 0.03 millimeters.

An important part of any fluid collection bag is in its ability to remain in the open position during the surgical procedure. If the bag collapses it will cease to properly drain the fluid. The foam support 12 solves this problem. Foam is a naturally resilient material and contains a "memory" in that it automatically reshapes to its original shape upon the release of pressure. In prior art fluid collection bags it is standard to use wire as the opening 24 support. Wire can break and must be continually reformed by hand to retain its proper shape. By using foam, the disadvantages of wire have been eliminated. The opening 24 will automatically stay in the open position, when a foam support is used.

While foam has been known in this art as an opening support material, as disclosed by the previously described patents, the present invention incorporates foam with a specific shape, density and texture. The improved foam support 12 is corrugated and placed continuously around the opening. The importance in the corrugated shape lies in its ability to continuously channel fluid to the fluid drainage ports 18. Even if the sidewall 20 collapses, and the form ring 12 makes contact with the base sheet 14, fluid flow will not be prevented. The ridges and valleys of the corrugated surface form a series of channels for the fluid. In prior art wire support rings, if the sidewall collapsed and the wire made contact with the base sheet, a dam would result and fluid would overflow, possibly leading to contamination of the patient and/or medical staff. This situation has been eliminated with the corrugated foam support ring 12. Fluid will flow between the ridges and continue to be accumulated or removed via the fluid discharge ports 18.

There are a variety of ways to secure the foam support ring to the sidewall sheet 20. A detail of one such way is shown in FIG. 4. Plastic bands 40 can be used to secure the foam support ring 12 to sidewall sheet 20. These plastic band 40 are constructed from the same material of the sidewall sheet 20, preferably a clear, medical grade polyethylene film. Alternate fastening means can be accomplished by the use of adhesive or by using adhesive in combination with the plastic band 40. Another way to secure the foam support to the sidewall sheet is shown in FIGS. 4a, 5, 6 and 7. The foam support 12, 58 can be completely enveloped by the sidewall material of preferably a clear medical grade polyethylene film. This has been found to be the most secure way to fasten the foam support 12, 58 to the fluid collection bag 10.

In operation of the present invention the release paper 28 is peeled away from adhesive 26, and the fluid collection bag 10 is placed on and adhered to the patient. The surgeon has access to the surgical site through the opening 24. The opening 24 is of such a diameter to allow unobstructed access to the surgical site. As fluid is generated during the surgical procedure it enters into the fluid collection bag 10 and can be accumulated therein or removed through fluid drainage ports 18. Upon completion of the surgical procedure, the fluid collection bag is easily removed from the patient and can be discarded.

Figure 5:
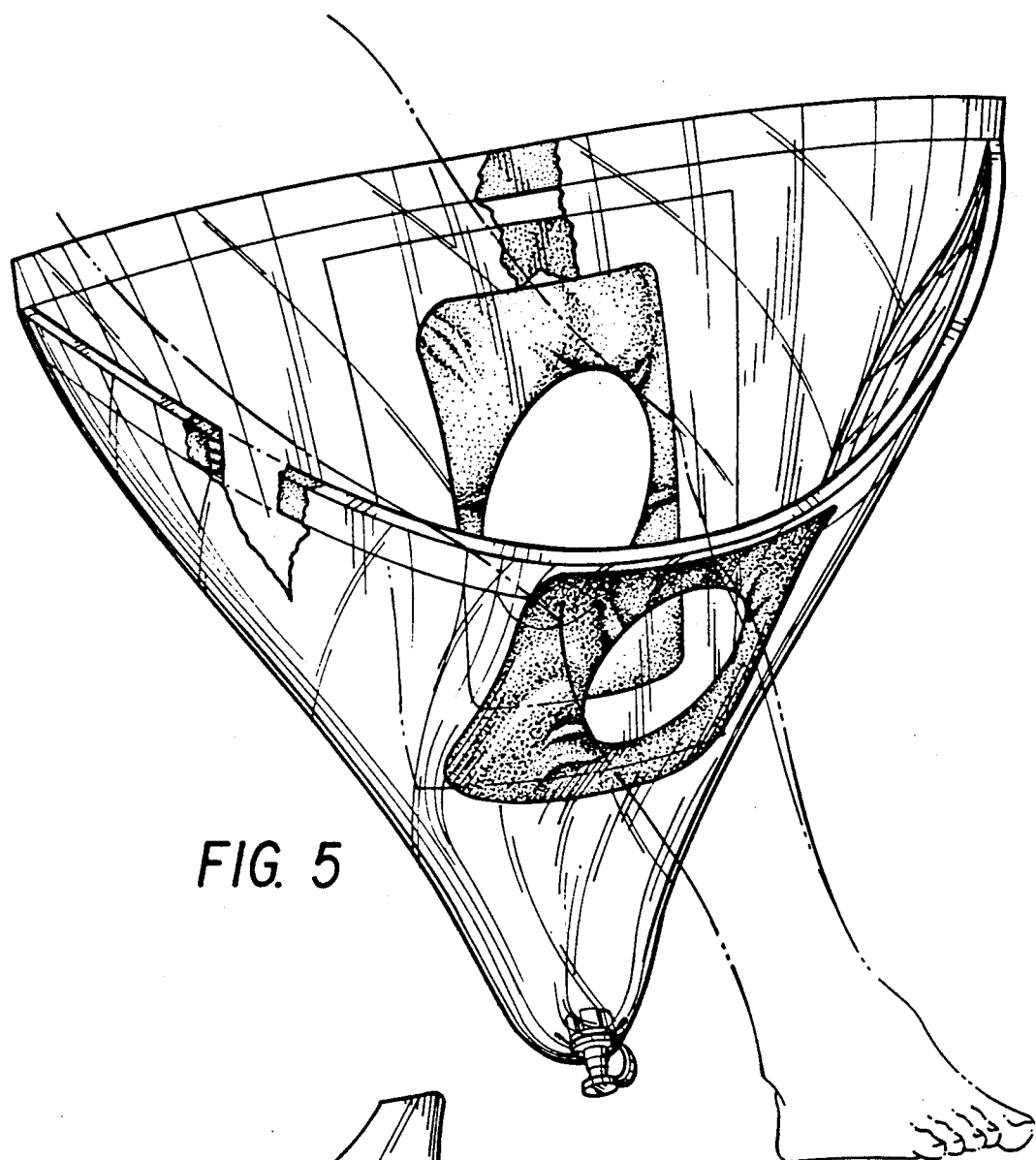
FIG. 5 is a perspective view, partly in section, of an alternate embodiment of the present invention for an orthopedic fluid collection bag.

FIG. 5 illustrates an alternate embodiment of the present invention for an orthopedic fluid collection bag. Fluid collection bag 10 is constructed of a fluid impervious plastic film material 50 with a flexible rubber panel 52 with circular opening 54. The opening 54 is maintained in the correct open position by foam bar 58. The plastic film material 50 completely envelopes and secures the foam bar 58. The foam bar 58 is constructed so as to continuously force the opening 56 into the correct open position. This allows for unobstructed access to the surgical site, shown in phantom by the outline of a knee. The bag is secured to the leg of the patient by the use of adhesive portions 26.

Figure 6:
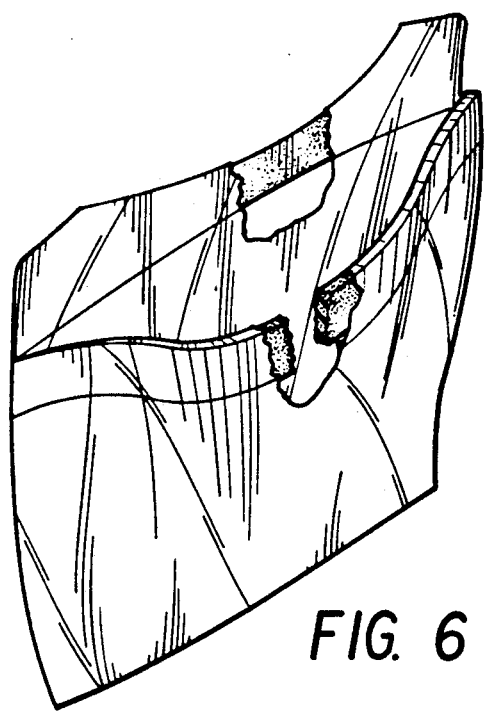
FIG. 6 is a perspective view, partly in section, of an alternate embodiment of the present invention for an eye or ear fluid collection bag.
Figure 7:
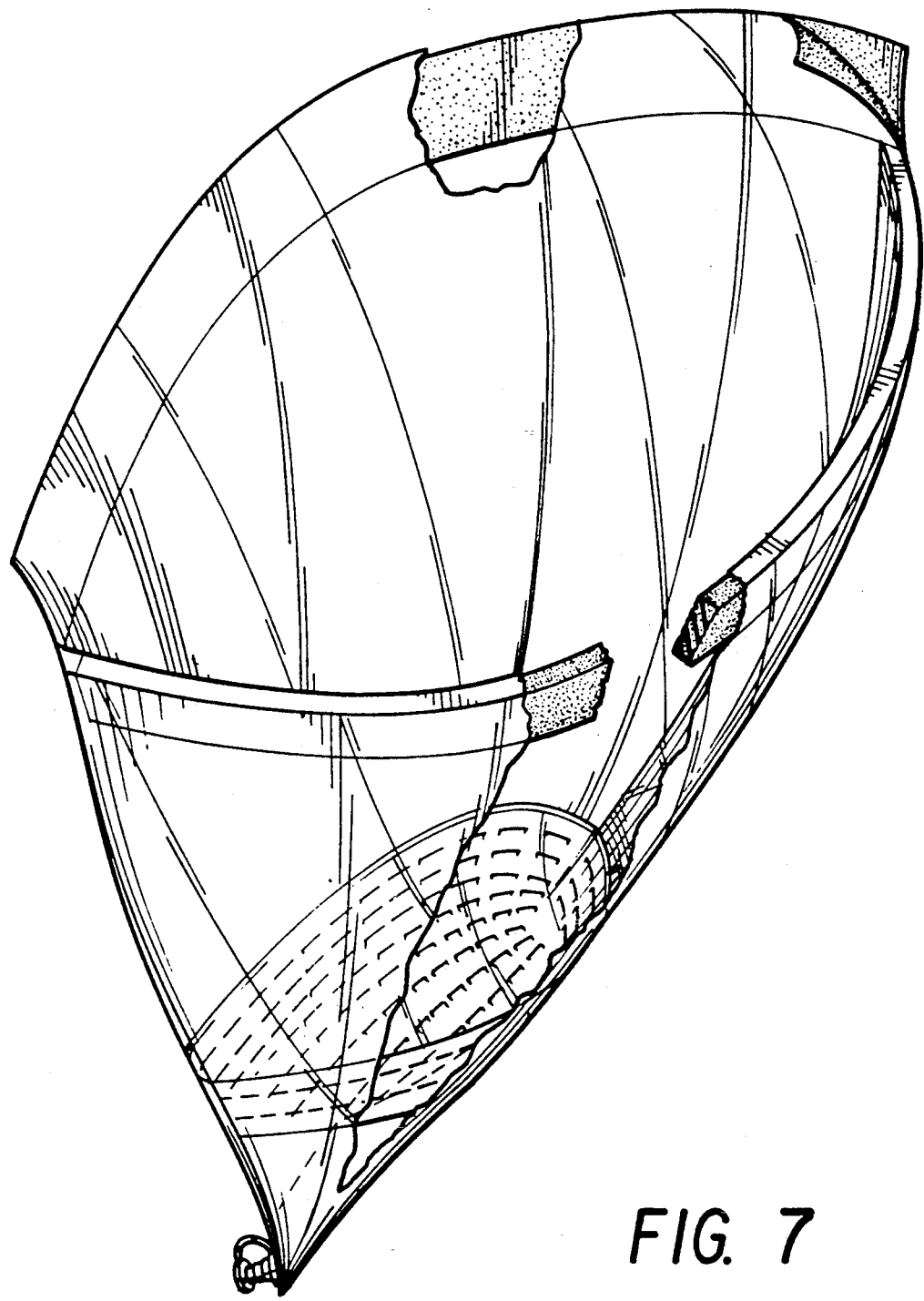
FIG. 7 is a perspective view, partly in section, of an alternate embodiment of the present invention for a universal fluid collection bag.

FIG. 6 shows another embodiment of the present invention for an eye or ear fluid collection bag 60. Foam bar 58 is specifically shaped so as to automatically keep the fluid collection bag 60 in the correct open position. FIG. 7 shows another embodiment of the present invention consisting of a universal fluid collection bag 70, with a filter 72 located in the lower portion of the bag. The filter 72 prevents the fluid discharge port 18 from becoming clogged with solids that may be generated during a surgical procedure. Preferably, the filter 72 is constructed of polyethylene film and contains a matrix of openings to allow drainable fluids to pass through filter 72 and be discharged by fluid discharge port 18.

It is to be understood that the present invention is not limited to the sole embodiment described above, but encompasses any and all embodiments within the scope of the following claims.

We claim:

1. A fluid collection bag comprising:
a base sheet constructed of a nonwoven flexible fabric;
a surgical site centrally located on said base sheet, through which a surgical procedure is performed;
at least one fluid discharge port provided in said base sheet for the removal of fluids accumulated during said surgical procedure;
a sidewall sheet, fastened to said base sheet and extending upward therefrom to substantially overlie said base sheet, said sidewall sheet constructed of a nonwoven flexible fabric, and provided with an opening above said surgical site, to allow a surgeon access to said surgical site through said opening;
reinforcing means maintaining said opening in an open position when said fluid collection bag is in its normal operating position, said reinforcing means comprising a flexible, continuous, resilient, polymeric foam rod, having opposite first and second surfaces;
fastening means securing said reinforcing means to said sidewall sheet adjacent said opening;
said first surface of said reinforcing means being disposed adjacent said sidewall sheet; and
said second surface of said reinforcing means is generally corrugated in shape with alternating ridges and valleys; whereby
fluid accumulated during said surgical procedure is channeled through the valleys and between the ridges of said second surface when said reinforcing means is in contact with said base sheet.

2. The fluid collection bag of claim 1 wherein: said sidewall sheet comprises a two layer sidewall sheet, whereby said two layer sidewall sheet provides additional protection from abrasion, punctures and tears.

3. The fluid collection bag of claim 1 including: pressure sensitive adhesive means on the bottom of said base sheet, in the area of said surgical site, and where contact between the patient and said fluid collection bag will occur.

4. The fluid collection bag of claim 1 wherein: said fastening means comprises nonwoven flexible fabric bands, spaced about the length of said reinforcing means and individually affixed to said sidewall sheet.

5. The fluid collection bag of claim 1 wherein: said fastening means comprises adhesive means, between said reinforcing means and said sidewall sheet.

6. The fluid collection bag of claim 1 wherein: said reinforcing means is enveloped by said nonwoven flexible fabric for securing said reinforcing means to said fluid collection bag.

7. A fluid collection bag comprising:
a fluid impervious sheet constructed of a nonwoven flexible fabric, including a base sheet, and a sidewall sheet fastened to said base sheet;
reinforcing means maintaining an opening, in said fluid collection bag, in an open position when said fluid collection bag is in its normal operating position, said reinforcing means comprising a flexible, resilient, polymeric foam rod;
fastening means, constructed of a nonwoven flexible fabric, securing said reinforcing means to said fluid impervious sheet adjacent said opening by completely enveloping said reinforcing means;
pressure sensitive adhesive means on said base sheet where contact between a patient and said fluid collection bag will occur;
at least one fluid discharge port provided in said fluid impervious sheet for the removal of fluids accumulated during a surgical procedure; and
filter means located inside said fluid collection bag, defining upper and lower cavities within said fluid collection bag, said filter means being constructed of a nonwoven flexible fabric, and is attached to said base sheet and said sidewall street for preventing the clogging of said at least one fluid discharge port.

* * * * *